United States Patent
Endrikat et al.

(10) Patent No.: US 6,995,149 B1
(45) Date of Patent: Feb. 7, 2006

(54) CONTRACEPTIVE PROCESS AND KIT FOR FEMALE MAMMALS, COMPRISING A COMBINATION OF GESTAGEN AND OESTROGEN

(75) Inventors: Jan Endrikat, Berlin (DE); Bernd Düsterberg, Berlin (DE); Pia Reilhac, Nantes (FR)

(73) Assignee: Schering AG, Berlin (DE)

( * ) Notice: Subject to any disclaimer, the term of this patent is extended or adjusted under 35 U.S.C. 154(b) by 0 days.

(21) Appl. No.: 09/091,665

(22) PCT Filed: Dec. 20, 1996

(86) PCT No.: PCT/DE96/02486

§ 371 (c)(1),
(2), (4) Date: Sep. 2, 1998

(87) PCT Pub. No.: WO97/23228

PCT Pub. Date: Jul. 3, 1997

(30) Foreign Application Priority Data

Dec. 23, 1995 (DE) .............................. 195 49 264.1

(51) Int. Cl.
*A61K 31/56* (2006.01)
*A01N 43/00* (2006.01)

(52) U.S. Cl. ...................... 514/170; 514/179; 514/181; 514/182

(58) Field of Classification Search ................. 514/170, 514/179, 181, 182, 180
See application file for complete search history.

(56) References Cited

U.S. PATENT DOCUMENTS

| | | | | | |
|---|---|---|---|---|---|
| 5,770,226 | A | * | 6/1998 | Hughes, Jr. et al. | 424/464 |
| 5,827,843 | A | * | 10/1998 | Koninckx | 514/170 |
| 5,888,543 | A | * | 3/1999 | Gast | 424/464 |
| 5,898,032 | A | * | 4/1999 | Hodgen | 514/178 |
| 5,972,377 | A | * | 10/1999 | Jona et al. | 424/449 |
| 6,139,873 | A | * | 10/2000 | Hughes, Jr. et al. | 424/464 |
| 6,433,251 | B1 | * | 8/2002 | Wagner et al. | 800/287 |
| 6,479,475 | B1 | * | 11/2002 | Gast | 514/170 |
| 6,831,073 | B1 | * | 12/2004 | Lanquetin et al. | 514/169 |
| 6,906,049 | B1 | * | 6/2005 | Paris et al. | 514/170 |

FOREIGN PATENT DOCUMENTS

| | | |
|---|---|---|
| CA | 2000438 | 4/1990 |
| EP | 0368373 | 5/1990 |

OTHER PUBLICATIONS

Neuman, Friedmund (CA 118:161077, abstract of Pharm. Zt. (1992), 137(34), 9-15).*
El-Sherbini, Abbas (CA 82:68681 abstract of Ain Shams Med. J. (1974), 25(4), 579-85).*
Weiner et al. (DN 86:12188, CAPLUS, abstract of Contraception (1976), 14(5), 551-62).*

* cited by examiner

*Primary Examiner*—Sabiha N. Qazi
(74) *Attorney, Agent, or Firm*—Millen, White, Zelano & Branigan, P.C.

(57) ABSTRACT

The present invention relates to a female mammal contraceptive process consisting of the sequential administration for at least 28 days of (a) a gestagen in an ovulation-preventing dose for at least 28 days in combination with (b) a natural oestrogen for 5 to 10 days at the end of the sequential dosage of at least 28 days, and a contraception kit.

64 Claims, No Drawings

CONTRACEPTIVE PROCESS AND KIT FOR FEMALE MAMMALS, COMPRISING A COMBINATION OF GESTAGEN AND OESTROGEN

This invention relates to a contraceptive process for female mammals that consists of at least 28 days of sequential administration of:

(a) a gestagen in an ovulation-inhibiting dose for at least 28 days, in combination with (b) a natural estrogen for 5 to 10 days at the end of the sequential administration of at least 28 days.

Since the 1960's, hormonal contraceptives have been known as, on the one hand, so-called combination preparations and stepped preparations and, on the other hand, sequential preparations. All of these preparations inhibit ovulation and produce regular menstrual bleeding (withdrawal bleeding).

Most hormonal contraceptives contain an estrogen and a gestagen (Table 1).

The different types of hormonal contraceptives.

| Nam | Composition |
| --- | --- |
| Combination preparation (one-phase preparation) of a stepped combination preparation | Estrogen and gestagen |
| Sequential preparation | Estrogen (1st phase) and estrogen/gestagen (2nd phase) |
| Minipill | Gestagen |
| Postcoital pill | Estrogen and gestagen |

Combination preparations are characterized by the fact that the dosages of the two hormonal components (estrogen/gestagen) remain the same. Combination preparations exhibit high contraceptive reliability owing to the simultaneous administration of the gestagen and estrogen components from the first day of administration. In all forms of the combination preparations, the ovulatory LH-apex is reliably suppressed in such a way that both ovulation and the formation of the corpus luteum are suppressed [Elstein, M. et al.: Studies on Low Dose Oral Contraceptives: Cervical Mucus and Plasma Hormone Changes in Relation to Circulating d-Norgestrel and 17-Ethinyl Estradiol Concentrations. Fertil. Sterl 27:892 (1976)]. The early secretory transformation of the poorly developed endometrium can lead to the occurrence of spotting (intracyclic menstrual bleeding), especially during the initial cycles when the preparations are taken.

To keep the gestagen dose low, so-called stepped combination preparations were developed. In this case, a distinction is made between two-stage and three-stage preparations. The two-stage preparations are distinguished in that the administration of gestagen is subdivided into two phases. In the first phase (11 days), a lower gestagen dose than in the second phase, with the same estrogen dose, is administered. In the three-stage preparations, the principle of stepped combination preparations was further refined; this is a modification of the two-stage preparation. Here, the gestagen dose is divided into three phases: the first phase contains a small gestagen dose, which is increased during the following two phases, while the estrogen dose is either constant over all three phases or is increased during the second phase.

Sequential preparations are distinguished in that they contain a pure estrogen component in the first 7 to at most 11 days of use, and they contain a gestagen component only in the subsequent 10 to at most 14 days. The influence of these preparations on the endometrium comes very close to the physiological cycle-dependent hormonal influence. The contraceptive reliability of the typical sequential preparations is based in the first phase only on the gonadotropin-inhibiting action of the estrogen, while the gestagen that is additionally taken during the second phase is mainly used for secretory transformation of the endometrium and for regular triggering of withdrawal bleeding.

Most oral contraceptives are administered over a period of 21 days, followed by 7 days of placebos or pill-free days, thus imitating a normal cycle.

In addition, pure gestagen preparations are known.

In early studies, it was shown that even very small doses of the gestagen chloromadinone acetate afforded contraceptive protection although ovulation is not always inhibited by the small gestagen dose [Martinez-Manautou, J., J. Giner-Velasquez, V. Gallegos-Cortès, J. Casasola, R. Aznar, H. Rudel: Fertility Control with Microdose of Progestogen. In C. Gual: Proc. VIth Pan-Amer. Conf. Endocr. Mexico City 1965. Exerpta Med. (Amst.) Int. Congr. Ser. No. 112, pp. 157–165; Rudel, H. W., J. Martinez-Manautou, M. Maqueo-Topete: The Role of Progesterogens in the Hormonal Control of Fertility. Fert. and Sterl. 16 (1965) 158–169).

The use of pure gestagen preparations for contraception became important again since it turned out that the estrogen component could be responsible for some undesirable accompanying phenomena (headache; nausea, weight gain, etc.) and mainly for dangerous complications such as thromboembolic diseases [Daniel, D. G., Campell, A. C. Turnbull: Perperalthromboembolism and Suppression of Lactation. Lancet 1967/II, 287–289].

Because of the low dosage, the pure gestagen preparations came to be called the minipill. The minipills that have been introduced to date are without exception derivatives of 19-nortestosterone: norethisterone, lynestrenol, and levonorgestrel. In contrast to estrogen/gestagen preparations, minipills are administered without interruption with regard to the time of bleeding since it was assumed that the unreliability of previously known pure gestagen preparations could be remedied if the administration period was extended.

The previously described pure gestagen preparations have a contraceptive reliability that is not very high; this can be attributed to the fact that ovulation is not always inhibited in a regular manner [Vessey et al.: Progestogen-Only Oral Contraception. Findings in Large Prospective Study with Special Reference to Effectiveness, Brit. J. Family Planning, 292: 526–30 (1986)]. In general, it can thus be expected that the proportion of anovulatory cycles is only between 15% and 40% under the influence of these low-dose gestagens [Chi, I.: The Safety and Efficacy of Progestin-Only Oral Contraceptives. An Epidemiologic Perspective. Contraception 47 (1993) 1–21].

Patent Application EP A 0 491 443 discloses a pure gestagen preparation in which the gestagens desogestrel and 3-ketodesogestrel are administered in a daily dose of 70 to 80 µg. In almost all women, these dosages cause inhibition of ovulation.

If gestagens alone are administered in ovulation-inhibiting doses, there is the risk, however, of amenorrhea, and in the case of prolonged administration, additional symptoms of hypoestrogeneity may occur.

There is therefore a need to ensure the advantages of a pure gestagen preparation combined with more reliable cycle control and regular menstrual-like bleeding.

It has now been found, surprisingly enough, that the administration of a gestagen in an ovulation-inhibiting amount for at least 28 days in combination with the administration of a natural estrogen, at the end of the cycle for 10 to 5 days, ensures optimum cycle control and regular menstrual-like bleeding.

This object is achieved in the above-described contraceptive process.

In a preferred embodiment of the inventive process, the mammals are humans.

In a preferred embodiment, the administration of the gestagen is done orally, and the administration of the natural estrogen is done transdermally. In another preferred embodiment, the administration of the gestagen is done transdermally, and the natural estrogen is administered orally.

In another embodiment, the invention relates to a contraceptive kit that contains at least 28 daily dosage units with
(a) a first phase that consists of at least 18 to 23 first daily dosage units of a gestagen in an ovulation-inhibiting dose, and
(b) a second phase that consists of at least 5 to 10 second daily dosage units of a gestagen in an ovulation-inhibiting dose, in combination with a natural estrogen.

Preferably, in all embodiments of the invention, the gestagen is selected from the group of compounds:
gestodene,
progesterone,
levonorgestrel,
cyproterone acetate,
chloromadinone acetate,
drospirenone (dihydrospirorenone),
norethisterone,
norethisterone acetate,
norgestimate,
desogestrel,
3-ketodesogestrel,
dienogest or a mixture thereof.

In a special embodiment, the gestagen is contained in a daily dosage of:
0.05–0.2 mg of levonorgestrel,
0.05–0.15 mg of gestodene or a bioequivalent dosage of another gestagen.

In a special embodiment, the gestagen levonorgestrel is contained in a daily dosage of 0.1 mg or gestodene in a daily dosage of 0.075 mg.

The inventive process combines the advantages of pure gestagen administration with more reliable cycle control and regular menstrual-like bleeding.

The gestagen ensures the contraceptive action, while the endometrium is built up by the natural estrogen, and in each case there is menstrual-like bleeding at the end of the combination phase.

This regimen exhibits the following advantages compared to the previously known processes for oral contraception:
Ovulation is effectively inhibited by a daily gestagen dose that is low but high enough.
Good cycle control is ensured by the sequential administration of natural estrogen.
Even for women in premenopause, this inventive contraceptive is well-tolerated owing to the use of a natural estrogen and yields positive effects, especially in bones.

Good general compatibility and especially liver-compatibility are ensured by the use of natural estrogen.

It results in significantly fewer ethinyl estradiol-related side-effects.

EXAMPLES

Examples of the inventive contraceptive process

Example 1

| |
|---|
| 10-day administration of 2.5 mg of estradiol per day |
| 28-day administration of 0.1 mg of levonorgestrel per day |

Example 2

| |
|---|
| 8-day administration of 2.5 mg of estradiol per day |
| 28-day administration of 0.1 mg of levonorgestrel per day |

Example 3

| |
|---|
| 10-day administration of 2.5 mg of estradiol per day |
| 56-day administration of 0.1 mg of levonorgestrel per day |

Example 4

| |
|---|
| 10-day administration of 2.5 mg of estradiol per day |
| 84-day administration of 0.1 mg of levonorgestrel per day |

Example 5

| |
|---|
| 10-day administration of 2.5 mg of estradiol per day |
| 28-day administration of 0.075 mg of gestodene per day |

Example 6

| |
|---|
| 8-day administration of 2.5 mg of estradiol per day |
| 28-day administration of 0.075 mg of gestodene per day |

Example 7

| |
|---|
| 10-day administration of 2.5 mg of estradiol per day |
| 56-day administration of 0.075 mg of gestodene per day |

Example 8

| | 10-day administration of 2.5 mg of estradiol per day |
|---|---|
| 84-day administration of 0.075 mg of gestodene per day | |

Other embodiments will emerge from the description of inventive activity.

Examples of the embodiment of the contraceptive kit

Example 1

| MO | TU | WE | TH | FR | SA | SU |
|---|---|---|---|---|---|---|
| • | • | • | • | • | • | • |
| • | • | • | • | • | • | • |
| • | • | • | • | • | • | • |
| ○ | ○ | ○ | ○ | ○ | ○ | ○ |

• = Gestagen-dosage unit (e.g., levonorgestrel 0.1 mg or gestodene 0.075 mg)
○ = Gestagen- and estrogen-dosage unit (e.g., levonorgestrel 0.1 mg/estradiol 2.5 mg or gestodene 0.075 mg/estradiol 2.5 mg))

Example 2

| MO | DI | MI | DO | FR | SA | SO |
|---|---|---|---|---|---|---|
| • | • | • | • | • | • | • |
| • | • | • | • | • | • | • |
| • | • | • | • | • | • | • |
| ○ | ○ | ○ | ○ | ○ | ○ | ○ |

(Three overlapping weekly tables as shown)

• = Gestagen-dosage unit (e.g., levonorgestrel 0.1 mg or gestodene 0.075 mg)
○ = Gestagen- and estrogen-dosage unit (e.g., levonorgestrel 0.1 mg/estradiol 2.5 mg or gestodene 0.075 mg/estradiol 2.5 mg))

Other embodiments of the inventive kit can be ascertained from the description.

The administration of the inventive process can be done locally, topically, enterally, transdermally, or parenterally.

For the preferred oral administration, tablets, coated tablets, capsules, pills, suspensions, or solutions, which can be produced in the usual way with the additives and vehicles that are commonly used in galenicals, are especially suitable.

For local or topical use, for example, vaginal suppositories, vaginal gels, implants, vaginal rings, or transdermal systems such as skin patches are suitable.

If the administration of the inventive process is done by an implant, a vaginal ring, or a transdermal system, these administration systems must be constituted in such a way that each day they release the dose for the respective form of administration that is equivalent in action to the daily oral dose.

For transdermal administration by a skin patch, the following gestagens are especially suitable: gestodene, levonorgestrel, desogestrel, 3-ketodesogestrel or a mixture thereof, and as natural estrogens: estradiol at a concentration of 0.025–0.25 mg of release rate per day. The release rate per day for the gestagens that are to be administered transdermally through a skin patch corresponds to the indicated daily dose concentrations.

The administration of the gestagen or the natural estrogen according to this invention can be done in such a way that both components are administered transdermally or else also that, for example, the gestagen is administered transdermally and the administration of the natural estrogen is done orally or, vice versa, the natural estrogen is administered transdermally and the gestagen orally.

The determination of equivalent-action doses of various gestagens and natural estrogens is done according to known methods; further details are found in, for example, the two articles "Probleme der Dosisfindung: Sexualhormone [Problems of Dose-Finding: Sex Hormones]"; F. Neumann et al., in "Arzneimittelforschung [Pharmaceutical Agent Research]" 27, 2a, 296–318 (1977) as well as "Aktuelle Entwicklungen in der hormonalen Kontrazeption [Current Developments in Hormonal Contraception]"; H. Kuhl in "Gynäkologe [Gynecology]" 25: 231–240 (1992).

We claim:

1. A method of contraception in a female mammal, comprising administering to said mammal a gestagen over a period of at least 28 days, wherein said period has a first phase and a second phase,
   wherein said first phase consists essentially of administering an ovulation-inhibiting amount of a gestagen, and said second phase comprises administering an ovulation-inhibiting amount of a gestagen and a natural estrogen in an amount effective to achieve regular menstrual-like bleeding,
   wherein said second phase is the last 5 to 10 days of said period and said first phase is the remainder of said period.

2. The method of claim 1, wherein said period is 28 days.

3. The method of claim 1, wherein in the second phase, the gestagen and natural estrogen are administered in combination.

4. The method of claim 1, wherein in the second phase, the gestagen and natural estrogen are administered separately.

5. The method according to claim 1, wherein the female mammal is human.

6. The method according to claim 1, wherein the gestagen is administered orally and the natural estrogen is administered transdermally.

7. The method according to claim 1, wherein the gestagen is administered transdermally and the natural estrogen is administered orally.

8. The method according to claim 1, wherein the gestagen and the natural estrogen are administered transdermally.

9. The method according to claim 1, wherein the gestagen is levonorgestrel or gestodene.

10. The method according to claim 1, wherein the gestagen is
    levonorgestrel in a dose of 0.05–0.2 mg/day, or
    gestodene in a dose of 0.05–0.15 mg/day.

11. The method according to claim 1, wherein the gestagen and natural estrogen are each independently administered locally, topically, enterally, transdermally and/or parenterally.

12. The method according to claim 1, wherein gestodene, levonorgestrel, desogestrel, 3-ketodesogestrol or a mixture thereof is administered transdermally, and estradiol is administered transdermally at a dose of 0.025–0.25 mg of release/day.

13. The method of claim 3, wherein
during the first phase, at least 18–23 first daily dosage units of a gestagen in an ovulation-inhibiting dose are administered, and
during the second phase, at least 5 to 10 second daily dosage units of a gestagen in an ovulation-inhibiting dose plus a natural estrogen are administered.

14. The method according to claim 13, wherein 28 daily dosage units are administered; during the first phase, 18 to 23 of said first daily dosage units of a gestagen are administered; and during the second phase, 5 to 10 of said second daily dosage units of a gestagen plus a natural estrogen are administered.

15. The method according to claim 13, wherein during the second phase, 10 daily dosage units of said gestagen plus estrogen are administered.

16. The method according to claim 3, wherein the gestagen in each phase, independently, is
gestodene,
progesterone,
levonorgestrel,
cyproterone acetate,
chloromadinone acetate,
drospirenone (dihydrospirorenone),
norethisterone,
norethisterone acetate,
norgestimate,
desogestrel,
3-ketodesogestrel,
dienogest,
or a mixture thereof.

17. The method according to claim 3, wherein the gestagen in each phase is, independently,
levonorgestrel in a dose of 0.1 mg/day,
gestodene in a dose of 0.075 mg/day, or
another gestagen in a bioequivalent dosage.

18. A method of contraception in a female mammal, comprising administering to said mammal a daily steroidal preparation over a period of at least 28 days, wherein
during the last 5–10 days of said period said mammal is daily administered a gestagen in an ovulation-inhibiting dose and a natural estrogen, and
during the rest of said period said mammal is daily administered a steroidal preparation consisting essentially of a gestagen in an ovulation-inhibiting dose.

19. A method of contraception in a female mammal, comprising administering daily to said mammal a steroidal preparation over a period of at least 28 days, wherein
during the last 5–10 days of said period said mammal is daily administered a gestagen in an ovulation-inhibiting dose and a natural estrogen in an amount which is effective for achieving regular menstrual-like bleeding, and
during the rest of said period said mammal is daily administered a steroidal preparation consisting essentially of gestagen in an ovulation-inhibiting dose.

20. The method according to claim 1, wherein the second phase is the last 10 days of said at least 28 day period.

21. The method according to claim 1, wherein the gestagen is
gestodene,
progesterone,
levonorgestrel,
cyproterone acetate,
chloromadinone acetate,
drospirenone (dihydrospirorenone),
norethisterone,
norethisterone acetate,
norgestimate,
desogestrel,
3-ketodesogestrel,
dienogest,
or a mixture thereof.

22. The method according to claim 1, wherein the gestagen is
levonorgestrol at 0.05–0.2 mg/day,
gestodene at 0.05–0.15 mg/day,
or another gestagen in a bioequivalent dose.

23. The method according to claim 1, wherein the gestagen is administered orally and/or transdermally.

24. The method according to claim 1, wherein the natural estrogen is administered orally and/or transdermally.

25. A method of providing contraception in a female mammal comprising administering a daily steroid preparation to said female mammal for a period of 28–84 days and said period has a first phase and a second phase, wherein the second phase is the last 5 to 10 days of said period and said first phase is the remainder of said period,
wherein during said first phase a gestagen is daily administered in an ovulation inhibiting amount without an estrogen, and during said second phase a natural estrogen and an ovulation-inhibiting amount of a gestagen and are administered daily.

26. A method according to claim 25, wherein the second phase is the last 8 to 10 days of said 28–84 day period.

27. A method according to claim 25, wherein said period is 28 days.

28. A method according to claim 25, wherein said period is 56 days.

29. A method according to claim 25, wherein said period is 84 days.

30. A method according to claim 25, wherein the gestagen is
gestodene,
progesterone,
levonorgestrel,
cyproterone acetate,
chloromadinone acetate,
drospirenone (dihydrospirorenone),
norethisterone,
norethisterone acetate,
norgestimate,
desogestrel,
3-ketodesogestrel,
dienogest,
or a mixture thereof.

31. A method according to claim 25, wherein the gestagen is levonorgestrol which is administered at a dosage of 0.05–0.2 mg/day or another gestagen administered at a bioequivalent dose.

32. A method according to claim 25, wherein the gestagen is gestodene which is administered at a dosage of 0.05–0.15 mg/day or another gestagen administered at in a bioequivalent dose.

33. A method according to claim 25, wherein the gestagen is administered orally and/or transdermally.

34. A method according to claim 25, wherein the natural estrogen is administered orally and/or transdermally.

35. A method according to claim 33, wherein the natural estrogen is administered orally and/or transdermally.

36. A method according to claim 25, wherein in the second phase, the gestagen and natural estrogen are administered in combination.

37. A method according to claim 25, wherein in the second phase, the gestagen and natural estrogen are administered separately.

38. A method according to claim 25, wherein the female mammal is human.

39. A method according to claim 25, wherein the gestagen is administered transdermally and the natural estrogen is administered orally.

40. A method according to claim 25, wherein the gestagen is levonorgestrel or gestodene.

41. A method according to claim 25, wherein the gestagen is levonorgestrel in a dose of 0.05–0.2 mg/day or gestodene in a dose of 0.05–0.15 mg/day.

42. A method according to claim 25, wherein gestodene, levonorgestrel, desogestrel, 3-ketodesogestrol or a mixture thereof is administered transdermally, and estradiol is administered transdermally at a dose of 0.025–0.25 mg of release/day.

43. A method of providing contraception in a female mammal comprising administering a daily steroid preparation to said female mammal for a period of 28–84 days, said period having a first phase and a second phase, wherein the second phase is the last 5 to 10 days of said period and said first phase is the remainder of said period, wherein during said first phase a gestagen is daily administered in an ovulation inhibiting amount and the daily amount of gestagen administered remains the same throughout the period, and during said second phase a natural estrogen and an ovulation-inhibiting amount of a gestagen are administered daily.

44. A method according to claim 1, wherein the gestagen is administered orally and/the natural estrogen is administered orally.

45. A method according to claim 18, wherein the gestagen is administered orally and/the natural estrogen is administered orally.

46. A method according to claim 19, wherein the gestagen is administered orally and/the natural estrogen is administered orally.

47. A method according to claim 25, wherein the gestagen is administered orally and/the natural estrogen is administered orally.

48. A method according to claim 43, wherein the gestagen is administered orally and/the natural estrogen is administered orally.

49. A method according to claim 1, wherein there is a menstrual bleeding at the end of said period.

50. A method according to claim 18, wherein there is a menstrual bleeding at the end of said period.

51. A method according to claim 19, wherein there is a menstrual bleeding at the end of said period.

52. A method according to claim 25, wherein there is a menstrual bleeding at the end of said period.

53. A method according to claim 25, wherein there is a menstrual bleeding at the end of said period.

54. A method according to claim 1, wherein the second phase is the last 8 to 10 days of said period.

55. A method according to claim 1, wherein said period is 28–84 days.

56. A method according to claim 1, wherein said period is 28–56 days.

57. A method according to claim 1, wherein said method consists essentially of administering to said mammal, during said first phase, an ovulation-inhibiting amount of a gestagen, and, during said second phase, administering an ovulation-inhibiting amount of a gestagen and a natural estrogen in an amount effective to achieve regular menstrual-like bleeding.

58. A method according to claim 57, wherein said natural estrogen is estradiol and said gestagen is gestodene,
progesterone,
levonorgestrel,
cyproterone acetate,
chloromadinone acetate,
drospirenone (dihydrospirorenone),
norethisterone,
norethisterone acetate,
norgestimate,
desogestrel,
3-ketodesogestrel,
dienogest,
or a mixture thereof.

59. A method according to claim 57, wherein said period is 28–84 days.

60. A method according to claim 57, wherein said period is 28–56 days.

61. A method according to claim 58, wherein said first phase is 18–23 days.

62. A method according to claim 58, wherein said period is 28–84 days.

63. A method according to claim 58, wherein said period is 28–56 days.

64. A method according to claim 58, wherein said first phase is 18–23 days.

* * * * *

UNITED STATES PATENT AND TRADEMARK OFFICE
CERTIFICATE OF CORRECTION

PATENT NO. : 6,995,149 B1 Page 1 of 1
APPLICATION NO. : 09/091665
DATED : February 7, 2006
INVENTOR(S) : Endrikat et al.

It is certified that error appears in the above-identified patent and that said Letters Patent is hereby corrected as shown below:

Column 8, line 23 reads "ovulation inhibiting" should read -- ovulation-inhibiting --
Column 8, line 25 reads "and are administered" should read -- are administered --
Column 8, line 57 reads "administered at in a" should read -- administered at a --
Column 9, line 26 reads "ovulation inhibiting" should read -- ovulation-inhibiting --
Column 9, line 32 reads "and/the" should read -- and the--
Column 9, line 35 reads "and/the" should read -- and the--
Column 9, line 38 reads "and/the" should read -- and the--
Column 9, line 41 reads "and/the" should read -- and the--
Column 9, line 44 reads "and/the" should read -- and the--
Column 10, line 5 reads "according to claim 25," should read -- according to claim 43, --

Signed and Sealed this

Thirtieth Day of January, 2007

JON W. DUDAS
*Director of the United States Patent and Trademark Office*